(12) United States Patent
Kodama

(10) Patent No.: US 10,369,342 B2
(45) Date of Patent: Aug. 6, 2019

(54) DRUG SOLUTION INJECTION DEVICE

(71) Applicant: TOPPAN PRINTING CO., LTD., Taito-ku (JP)

(72) Inventor: Yoshihiro Kodama, Taito-ku (JP)

(73) Assignee: TOPPAN PRINTING CO., LTD., Taito-ku (JP)

(*) Notice: Subject to any disclaimer, the term of this patent is extended or adjusted under 35 U.S.C. 154(b) by 0 days.

(21) Appl. No.: 15/401,165

(22) Filed: Jan. 9, 2017

(65) Prior Publication Data

US 2017/0113030 A1  Apr. 27, 2017

Related U.S. Application Data

(63) Continuation of application No. PCT/JP2015/067618, filed on Jun. 18, 2015.

(30) Foreign Application Priority Data

Jul. 9, 2014 (JP) .................................. 2014-141238

(51) Int. Cl.
*A61M 5/32* (2006.01)
*A61M 37/00* (2006.01)

(52) U.S. Cl.
CPC ...... *A61M 37/0015* (2013.01); *A61M 5/3298* (2013.01); *A61M 37/00* (2013.01); *A61M 2037/003* (2013.01); *A61M 2037/0023* (2013.01); *A61M 2037/0061* (2013.01); *A61M 2205/02* (2013.01)

(58) Field of Classification Search
CPC .............. A61M 37/0015; A61M 37/00; A61M 5/3298; A61M 2037/0023; A61M 2037/003; A61M 2037/0061; A61M 2205/02
See application file for complete search history.

(56) References Cited

U.S. PATENT DOCUMENTS 7,842,008 B2  11/2010  Clarke et al.
8,419,684 B2   4/2013  Clarke et al.
9,452,257 B2   9/2016  Clarke et al.
(Continued)

FOREIGN PATENT DOCUMENTS

JP  2005-021677 A  1/2005
JP  2009-516572 A  4/2009
(Continued)

OTHER PUBLICATIONS

International Search Report dated Sep. 1, 2015 in PCT/JP2015/067618, filed Jun. 18, 2015.

*Primary Examiner* — Laura A Bouchelle
*Assistant Examiner* — Dung T Ulsh
(74) *Attorney, Agent, or Firm* — Oblon, McClelland, Maier & Neustadt, L.L.P.

(57) ABSTRACT

An injection device including a microneedle structure including a substrate having a first surface and a second surface opposite to the first surface, and a protrusion protruding from the first surface in a direction opposite to the second surface, the protrusion having a through hole which penetrates from a tip of the protrusion to the second surface in the direction of the protrusion such that a liquid flows through the through hole, and one or more check valves positioned to stop the liquid flowing from the second surface.

20 Claims, 4 Drawing Sheets

(56) References Cited

U.S. PATENT DOCUMENTS

| | | | | |
|---|---|---|---|---|
| 2003/0050602 A1* | 3/2003 | Pettis | | A61M 5/28 604/117 |
| 2005/0119618 A1* | 6/2005 | Gonnelli | | A61M 5/1452 604/150 |
| 2007/0129714 A1* | 6/2007 | Elkins | | A61B 18/02 606/21 |
| 2009/0042970 A1* | 2/2009 | Herschkowitz | | A61M 37/0015 514/423 |
| 2009/0221948 A1* | 9/2009 | Szamosfalvi | | A61M 1/3672 604/6.07 |
| 2009/0274566 A1* | 11/2009 | Fong | | F04B 53/1032 417/307 |
| 2011/0172601 A1* | 7/2011 | Beebe | | A61M 37/0015 604/131 |
| 2012/0035543 A1* | 2/2012 | Kamen | | A61M 5/14244 604/113 |
| 2012/0046644 A1* | 2/2012 | Ziaie | | A61M 5/14248 604/507 |
| 2012/0123387 A1 | 5/2012 | Gonzalez et al. | | |
| 2013/0090633 A1* | 4/2013 | Loeb | | A61K 9/0004 604/892.1 |
| 2013/0144257 A1* | 6/2013 | Ross | | A61M 37/0015 604/506 |
| 2014/0052067 A1* | 2/2014 | Sausse | | A61M 37/0015 604/173 |
| 2015/0094664 A1* | 4/2015 | Mizukoshi | | A61M 37/0015 604/150 |
| 2015/0157809 A1* | 6/2015 | Park | | A61M 5/204 604/131 |
| 2016/0106584 A1* | 4/2016 | Andino | | A61F 9/0017 604/87 |
| 2017/0007812 A1* | 1/2017 | Onozuka | | A61M 37/0015 |
| 2017/0021152 A1* | 1/2017 | Kodama | | A61M 5/44 |
| 2017/0113030 A1* | 4/2017 | Kodama | | A61M 37/0015 |
| 2017/0239457 A1* | 8/2017 | Asai | | A61M 37/0015 |
| 2017/0281919 A1* | 10/2017 | Asai | | A61M 37/0015 |

FOREIGN PATENT DOCUMENTS

| | | |
|---|---|---|
| JP | 2012-071092 A | 4/2012 |
| JP | 2013-500773 A | 1/2013 |
| JP | 2013-516274 A | 5/2013 |
| JP | 5550775 B1 | 7/2014 |
| JP | 2014-200352 A | 10/2014 |

* cited by examiner

DRUG SOLUTION INJECTION DEVICE

CROSS-REFERENCE TO RELATED APPLICATIONS

The present application is a continuation of International Application No. PCT/JP2015/067618, filed Jun. 18, 2015, which is based upon and claims the benefits of priority to Japanese Application No. 2014-141238, filed Jul. 9, 2014. The entire contents of these applications are incorporated herein by reference.

BACKGROUND OF THE INVENTION

Field of the Invention

The present invention relates to a drug solution injection device for use in administrating a drug solution by using a microneedle.

Discussion of the Background

Methods of administering a drug, such as a vaccine, into the body include a well-known method making use of a microneedle (e.g., refer to PTL 1). Such a microneedle has a plurality of protrusions, each having a needle-shape, on a surface of a substrate. In the administration method using a microneedle, protrusions pierce the skin by the substrate being pressed against the skin, and the drug is fed into the skin from holes formed by the protrusions. The length of the protrusions is restricted to a length which does not reach the nerve cells of the dermal layer in the skin. Thus, in the administration method using a microneedle, pain is alleviated when the skin is pierced, compared to the administration method using an injection needle. Further, the administration method using a microneedle administers a drug into an intradermal area where antigen-presenting cells are abundantly present. Therefore, dosage of the drug can be reduced compared to a subcutaneous injection.

A drug administration method using a microneedle uses a microneedle in which a through hole is formed penetrating a substrate and a protrusion in a direction in which the protrusion extends, and a drug solution, which is a liquid drug, is intradermally administered through the through hole. Normally, when administering a drug solution by such a method, a device such as an applicator is used to assist the protrusion piercing the skin and the drug solution being fed into the through hole.

For example, there is a proposed device which is provided with a limiter for controlling the insertion depth of the protrusion into the skin, and a stabilizer for restraining the distortion of the skin around the protrusion, for the purpose of preventing a part of a drug solution from leaking to the skin surface or leaking subcutaneously during administration of the drug solution (refer to PTL 2). For example, there is another proposed device in which a spring is assembled around the microneedle to urge the protrusion to puncture the skin, and prevent the protrusion from being detached from the skin during administration of a drug solution (refer to PTL 3).

PTL 1: JP-A 2005-21677
PTL 2: JP-A 2009-516572
PTL 3: JP-A 2013-500773

SUMMARY OF THE INVENTION

According to one aspect of the present invention, an injection device including a microneedle structure including a substrate having a first surface and a second surface opposite to the first surface, and a protrusion protruding from the first surface in a direction opposite to the second surface, the protrusion having a through hole which penetrates from a tip of the protrusion to the second surface in the direction of the protrusion such that a liquid flows through the through hole, and one or more check valves positioned to stop the liquid flowing from the second surface.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE EMBODIMENTS

Figure 1:
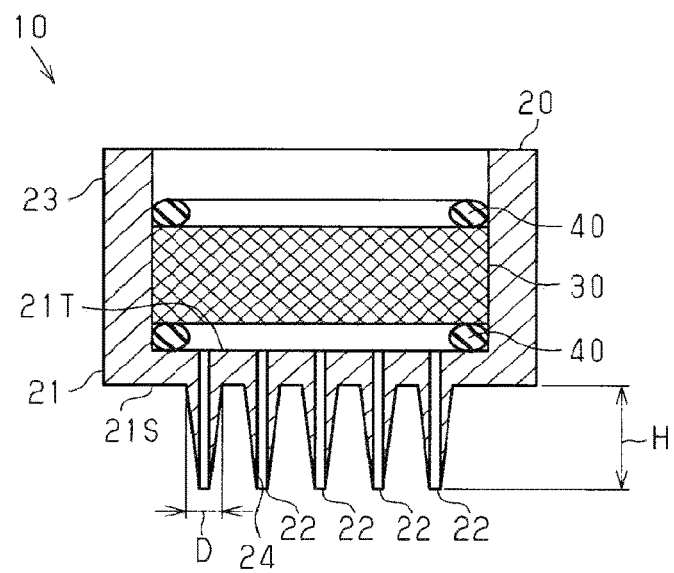
FIG. 1 is a cross-sectional view illustrating a cross-sectional structure of a drug solution injection device, according to an embodiment.

The embodiments will now be described with reference to the accompanying drawings, wherein like reference numerals designate corresponding or identical elements throughout the various drawings.

With reference to FIGS. 1 to 4, an embodiment of a drug solution injection device will be described.

Configuration of Drug Solution Injection Device

As shown in FIG. 1, a drug solution injection device 10 includes a microneedle structure 20, a check valve 30, and a seal member 40.

The microneedle structure 20 is provided with a plate-like substrate 21, a protrusion 22 protruding from the substrate 21, and a cylindrical part 23 extending from the substrate 21 in a direction opposite to the protrusion 22. The substrate 21, the protrusion 22, and the cylindrical part 23 are integrally formed.

The substrate 21 is in a disk shape, for example, and has a first surface 21S which is the surface formed with the protrusion 22, and a second surface 21T which is the surface on the opposite side of the first surface 21S, i.e. the surface to which the cylindrical part 23 is connected. The protrusion 22 protrudes from the first surface 21S in a direction opposite to the second surface 21T. The first surface 21S supports the base end of the protrusion 22.

Preferably, the protrusion 22 is finely formed with a tip angle sufficient for puncturing the skin as an administration target of the drug solution, and furthermore, has a length sufficient for permitting the drug solution to permeate into the skin. Namely, the protrusion 22 preferably has a shape in which the cross section becomes smaller towards the tip. For example, the protrusion 22 is formed into a conical shape or a pyramid shape. Alternatively, for example, the protrusion 22 may be in a shape that is a combination of two or more assemblies, such as a shape obtained by stacking a cone on a cylinder. The protrusion 22 may have a side wall formed with a constriction or a step.

The protrusion 22 has a length H from the first surface 21S of the substrate 21 to the tip of the protrusion 22. The length H is preferably a length that allows the protrusion 22 to penetrate the stratum corneum which is the outermost layer of the skin, and not to reach the neural layer. Specifically, the length H is preferably in the range of approximately from 100 μm to 3 mm. Further, the protrusion 22 has a width D in a direction parallel to the first surface 21S. The width D is preferably in the range of approximately from 10 μm to 800 μm.

The number of protrusions 22 can be optionally determined as long as the number is one or more. However, if a plurality of protrusions 22 are provided, the amount of drug solution which can be administered at one time can increase. Further, when the dosage of the drug solution is not increased, the administration period can be shortened by administering the drug solution dispersed in the plurality of protrusions 22.

It should be noted that the amount of the drug solution which can be administered at one time using the drug solution injection device 10 of the present embodiment is in the range of 0.05 ml or mote to 1 ml or less.

When the microneedle structure 20 has a plurality of protrusions 22, the plurality of protrusions 22 may be arranged regularly or irregularly on the first surface 21S of the substrate 21. For example, the plurality of protrusions 22 can be arranged in a lattice or concentric pattern as seen from the direction perpendicular to the first surface 21S.

The microneedle structure 20 is formed with a through hole 24 which penetrates from the tip of the protrusion 22 to the second surface 21T of the substrate 21 along the direction in which the protrusion 22 extends. The drug solution passes through the through hole 24 from the second surface 21T to the tip of the protrusion 22 and intradermally enters into the skin as an administration target.

The cylindrical part 23 extends from the second surface 21T of the substrate 21 in a direction opposite to the protrusion 22. The outer peripheral surface of the cylindrical part 23 substantially coincides with the outer peripheral edge of the second surface 21T. The cylindrical part 23 defines a space therein for communicating with the through hole 24. For example, when the substrate 21 has a disk shape, the cylindrical part 23 is formed into a cylindrical shape. In such a configuration, the cylindrical part 23, together with the second surface 21T of the substrate 21, configures a drug solution channel for communicating with the through hole 24.

Of the two ends of the cylindrical part 23, the end opposite to the substrate 21 is open, to which a drug solution supply instrument, such as a syringe, is mounted to inject a drug solution into the inner space of the cylindrical part 23 and the through hole 24. The open end of the cylindrical part 23 has a structure suitable for coupling with the drug solution supply instrument.

The microneedle structure 20 is preferably made of a biocompatible material. Examples of the biocompatible material include metals such as stainless steel, titanium, manganese and silicon, ceramics such as alumina, zirconia, silicon carbide and silicon nitride, medical silicones, polylactic acid, polyglycolic acid, and polycarbonate, or resins such as PEEK materials.

The method of producing the microneedle structure 20 is not specifically limited, and various well-known technologies may be used as the production method. For example, when using a resin as the formation material of the microneedle structure 20, the exterior shapes of the substrate 21, the protrusion 22, and the cylindrical part 23 are formed by molding technologies, such as injection molding, extrusion molding, imprinting, hot embossing, and casting, followed by forming the through hole 24 by use of a micro drill, a laser, or the like.

The check valve 30 is arranged on the inside of the cylindrical part 23, and serves to prevent the drug solution from flowing from the second surface 21T of the substrate 21 towards the check valve 30, i.e., from the protrusion 22 towards the open end of the cylindrical part 23. The configuration of the check valve 30 is not specifically limited as long as the configuration allows the liquid to flow from the open end of the cylindrical part 23 towards the second surface 21T of the substrate 21, and prevents the liquid from flowing from the second surface 21T towards the open end, on the inside of the cylindrical part 23. Examples of such a configuration of the check valve 30 include configurations of a spring disc type, a valve shaft type, a swing type, a wafer type, a lift type, a ball type, a foot valve, and the like. Specifically, the spring disc type and the valve shaft type check valves, which are simple in the structure, are suitable for being arranged in a small space inside the cylindrical part 23.

The check valve 30 is preferably structured so that the channel is opened upon reception of a forward pressure in the range of 0.01 MPa or more to 0.30 MPa or less. When the pressure of the drug solution is 0.01 MPa or more, the drug solution can be smoothly discharged from the tip of the protrusion 22 into the skin, even when influenced by the intradermal resistance or the like in administering the drug solution. On the other hand, when the pressure of the drug solution is 0.30 MPa or less, the pain caused in intradermally injecting the drug solution is minimized.

On the other hand, it is preferable that the check valve 30 is mechanically structured to close the channel upon reception of a reverse pressure in the range of 0.05 MPa or more to 0.30 MPa or less. When the injection pressure of the drug solution is 0.05 MPa or more, backflow easily occurs in the drug solution. Therefore, when the valve mechanism is structured to close the channel upon reception of a reverse pressure of 0.05 MPa or more, the effect of the embodiments of the present invention is enhanced. On the other hand, when the injection pressure of the drug solution is 0.30 MPa or less, the drug solution injection device 10 receives a reaction force upon release of the pressing force on the drug solution to thereby prevent detachment of the microneedle structure 20 from the skin.

The inventor found that when a physiological saline solution was used as the drug solution and when the injection pressure of the drug solution exceeded 0.05 MPa in the intradermal injection, the drug solution might flow back from inside the skin towards a syringe 50 mounted to the open end of the cylindrical part 23, accompanying the termination of pressure supply for the drug solution injection.

Therefore, it is preferable that the check valve 30 in the drug solution injection device 10 operates in the pressure range mentioned above, and the configuration of each of the parts of the drug solution injection device 10 is designed in conformity with the operation pressure. Specifically, it is preferable to use a check valve 30 operating within a range of 0.01 MPa or more to 0.30 MPa or less.

A well-known method may be used as a method of mounting the check valve 30 to the cylindrical part 23. For example, the check valve 30 can be mounted to the inner wall of the cylindrical part 23 by a method such as pressure-fixing by application of a pressure, or fixing by means of a sealing material, such as an adhesive agent. Further, the check valve 30 may be mounted to the inner wall of the cylindrical part 23 by the engagement of internal threads and external threads respectively formed on the check valve 30 and the inner wall of the cylindrical part 23.

Materials used for the member configuring the check valve 30 are not specifically limited. Examples of such materials include plastic, glass, ceramics, metals, elastomers and the like. Specifically, plastic materials include polyethylene, polypropylene, polystyrene, polyamide, polycarbonate, cyclic polyolefin, acrylic, urethane resins, epoxy resins, and the like.

Figure 2:
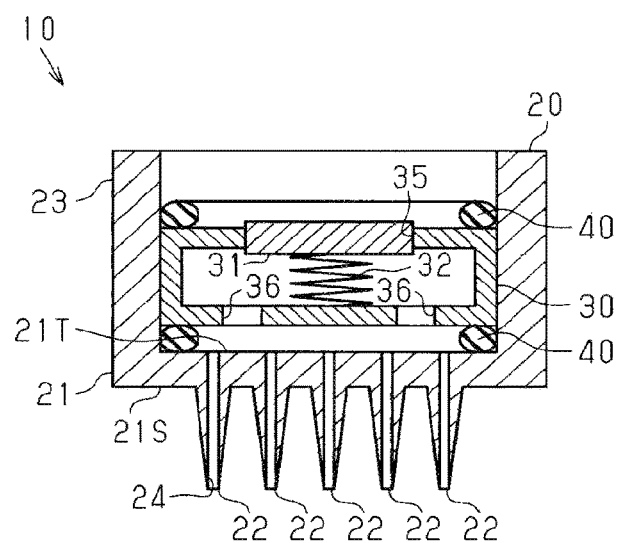
FIG. 2 is a cross-sectional view illustrating an example of a structure of a check valve, according to an embodiment.
Figure 3:
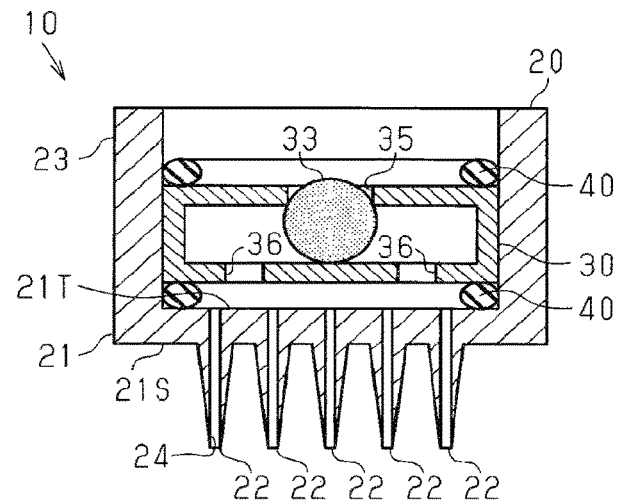
FIG. 3 is a cross-sectional view illustrating an example of a structure of a check valve, according to an embodiment.

FIG. 2 shows an example of a configuration of the drug solution injection device 10 that uses a spring disc type check valve as the check valve 30. FIG. 3 shows an example of a configuration of the drug solution injection device 10 that uses a valve shaft type check valve as the check valve 30.

In the example shown in FIG. 2, the check valve 30 includes a housing. The housing is in a box shape and includes an upstream channel and a downstream channel. The upstream channel is an inflow port 35 opened in a direction of the channel between the check valve 30 and the open end of the cylindrical part 23. The downstream channel is an outflow port 36 opened in a direction of the channel between the substrate 21 and the check valve 30. The check valve 30 is provided, within the housing, with a disk 31 which is a valve body, and a spring 32 which constantly urges the disk 31 towards the open end of the cylindrical part 23. The spring 32 is arranged on the downstream side relative to the disk 31, while the disk 31 closes the inflow port 35.

In such a configuration, the check valve 30 permits the drug solution to flow in a direction from the open end of the cylindrical part 23 to the second surface 21T of the substrate 21. Namely, the disk 31 is pressed against the spring 32 by the pressure of the drug solution passing through the open end of the cylindrical part 23 to thereby contract the spring 32. As a result, the disk 31 opens the inflow port 35, so that the channels on the upstream and downstream sides of the check valve 30 communicate with each other. On the other hand, the check valve 30 prevents the drug solution from flowing from the second surface 21T of the substrate 21 towards the open end of the cylindrical part 23. Namely, the disk 31 is pressed in a direction opposite to the spring 32 due to the pressure of the drug solution within the housing to thereby close the inflow port 35 with such a pressing force and the restoring force of the spring 32. Thus, the drug solution within the housing is prevented from flowing towards the open end of the cylindrical part 23, i.e. backflow of the drug solution is prevented in the through hole 24.

In the example shown in FIG. 3, the check valve 30 has a housing. The housing is in a box shape and formed with an inflow port 35 opened in a direction of the channel on the upstream side, and an outflow port 36 opened in a direction of the channel on the downstream side. The check valve 30 is provided, inside the housing, with an elastic ball 33 which is a valve body, with the surface of the elastic ball 33 closing the inflow port 35.

In such a configuration, the check valve 30 permits the drug solution to flow from the open end of the cylindrical part 23 towards the second surface 21T of the substrate 21. Namely, the elastic ball 33 is compressed towards the interior of the housing by the pressure of the drug solution passing through the open end of the cylindrical part 23 to open the inflow port 35, thereby allowing the channels on the upstream and downstream sides of the check valve 30 to communicate with each other. On the other hand, the check valve 30 prevents the drug solution from flowing from the second surface 21T of the substrate 21 towards the open end of the cylindrical part 23. Namely, the elastic ball 33 is restored and pressed against the inflow port 35 by the pressure of the drug solution within the housing to close the inflow port 35. Thus, the drug solution within the housing is prevented from flowing towards the open end of the cylindrical part 23, i.e. backflow of the drug solution is prevented in the through hole 24.

The check valve 30 is preferably arranged so that the surface of the housing formed with the inflow port 35 is parallel with the second surface 21T of the substrate 21. Namely, the body of the check valve 30 is preferably arranged so as to abut on the surface of the member formed with the inflow port 35 and close the channel, the surface of the member being perpendicular to the channel. With this configuration, the check valve 30 is prevented from excessively obstructing the forward flow of the drug solution, and at the same time, the drug solution is suitably prevented from flowing in the opposite direction.

The check valve 30 may be configured by a valve body, and a member for forming the channel which is closed by the valve body, with the omission of the housing. In this case, the valve body and the member may be arranged on the inside of the cylindrical part 23 to prevent the drug solution from flowing from the second surface 21T of the substrate 21 towards the check valve 30. For example, in the check valve 30 described with reference to FIG. 2, the spring 32 may be supported on the second surface 21T, and the plate-like member formed with the inflow port 35 and fixed to the inner wall of the cylindrical part 23 may be arranged between the disk 31 and the open end of the cylindrical part 23. Further, for example, in the check valve 30 described with reference to FIG. 3, the elastic ball 33 may be supported on the second surface 21T, and the plate-like member formed with the inflow port 35 and fixed to the inner wall of the cylindrical part 23 may be arranged between the elastic ball 33 and the open end of the cylindrical part 23.

The seal member 40 is annularly formed in the cylindrical part 23 so as to be concentric therewith, and located contacting the outer peripheral portion of the check valve 30. In the check valve 30, the seal member 40 is arranged on the surface opposed to the open end of the cylindrical part 23 and the surface opposed to the second surface 21T of the substrate 21. The seal member 40 arranged on the surface opposed to the second surface 21T is sandwiched between the second surface 21T and the check valve 30, and encloses all of the openings of the through holes 24 formed in one or more protrusions 22. Namely, the check valve 30 is arranged directly above the second surface 21T of the substrate 21 intervened by the seal member 40.

The two seal members 40 each prevent the drug solution from passing between the outer peripheral surface of the check valve 30 and the inner wall of the cylindrical part 23. The seal members 40 may be made of a material capable of preventing permeation of liquids, for example, embodied as an O-ring or a gasket.

Example of Use of the Drug Solution Injection Device

Figure 4:
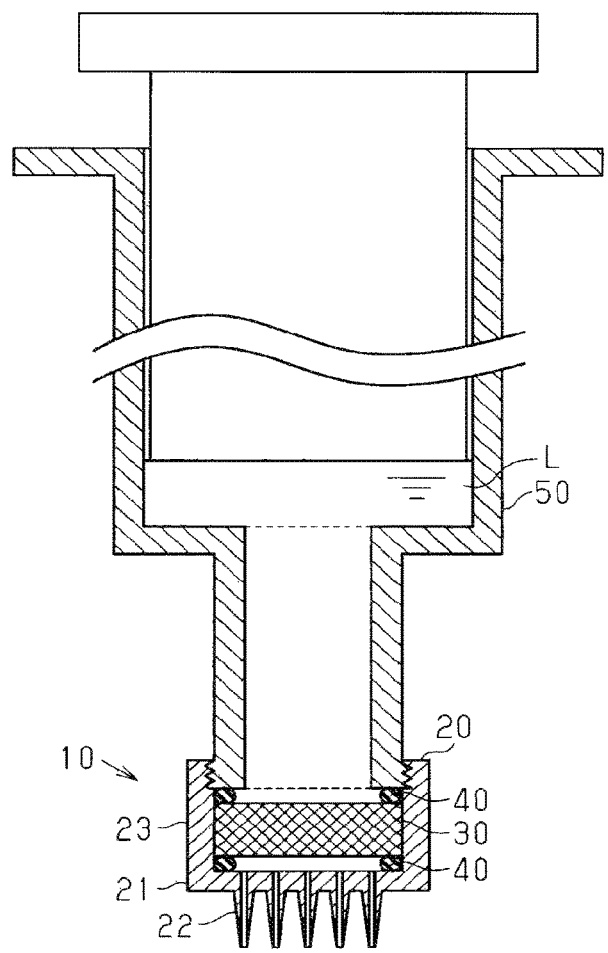
FIG. 4 is a cross-sectional view illustrating a drug solution injection device, i.e. a cross-sectional structure of a drug solution injection device assembled with a drug solution supply instrument, according to an embodiment.

As shown in FIG. 4, the syringe 50 may be mounted to the open end of the cylindrical part 23 of the drug solution injection device 10 to supply a drug solution L from the syringe 50 into the inner space of the cylindrical part 23 and into the through hole 24. When mounting the syringe 50 to the open end of the cylindrical part 23, the cylindrical part 23 can be connected to the syringe 50 by, for example, luer-slip or luer-lock connection.

The type of the drug solution L is not specifically limited as long as it is a liquid which exerts function when intradermally administered. Examples of the drug solution L that can be used include pharmacologically active substances such as vaccines and cosmetic compositions having an aesthetic effect.

A syringe for subcutaneous injection may be used as the syringe 50. Such syringes are available at low cost. Since the outer cylinder of the syringe 50 for subcutaneous injection is substantially transparent, the amount of the drug solution retained inside the syringe 50 can be viewed from outside. Further, since the scale for indicating the amount of a drug solution is provided on the outer surface of the outer cylinder, the amount of the drug solution retained inside the syringe 50 can be easily and accurately adjusted.

Preferably, the portions of the drug solution injection device 10 and the syringe 50 contacting the drug solution L are made of a material which does not alter or is not altered by the drug solution L, or the portions are coated with such a material.

Further, the drug solution injection device 10 or the syringe 50 may be assembled with a drive mechanism that includes a motive power source for imparting a force to the protrusion 22 to urge the protrusion 22 to puncture the skin as an administration target, and a motive power source for supplying the drug solution retained inside the syringe 50 into the inner space of the cylindrical part 23 and into the through hole 24.

For example, the drive mechanism may include a compression spring, a tensile spring, an elastic material, or a magnet as the motive power source, or may be a compressed gas drive mechanism which utilizes compressed air to generate motive power, or may be a drive mechanism which generates motive power by electric power. Furthermore, the drive mechanism may include a switch mechanism which controls operation of the motive power source and transmission of the motive power. For example, a latching mechanism, a trigger mechanism or a press clasp mechanism can be used as the switch mechanism. In these mechanisms, a stopper, whose movement is stopped against the force produced from the motive power source, is released by the release of the latch, the triggering of the trigger, or the pressing of the push clasp or push button, resultantly transmitting the motive power to the drug solution injection device 10 and the syringe 50. Further, when the drive mechanism is a compressed gas drive mechanism, the switch mechanism may include an on-off valve for controlling the supply of the compressed gas from the compressed gas supply source. This kind of valve may be a valve enabling manual switching between on and off, or may be a valve enabling electromagnetic driving.

Other than the aforementioned mechanisms, the drug solution injection device 10 or the syringe 50 may be used together with various operation assisting instruments, and drug solution supply assisting devices. Such a device is detachably fixed, for example, to the cylindrical part 23, the check valve 30, the outer cylinder of the syringe 50, or the outer surface of the piston, by means of a fixing member such as a screw or a clip.

The drug solution injection device 10 may be mounted with an instrument different from the syringe 50, as a drug solution supply instrument for supplying a drug solution to the drug solution injection device 10. For example, a drug solution supply instrument made exclusively for supplying a drug solution to the drug solution injection device 10 may be used.

Further, in the present embodiment, the administration target for a drug solution is not specifically limited, but may be animals including human beings.

Advantageous Effects

Advantageous effects of the drug solution injection device 10 of the present embodiment will be described.

As stated above, the drug solution injection device 10 has a drug solution channel provided with the check valve 30 for preventing the drug solution from flowing from the second surface 21T of the substrate 21 towards the check valve 30. Thus, the drug solution is prevented from flowing in a direction away from the skin that is an administration target for the drug solution, i.e. away from the tip of the protrusion 22. Therefore, when the pressing force of the drug solution directed to the tip of the protrusion 22 is released, backflow of the drug solution is prevented in the protrusion 22. As a result, the drug solution can be administered to the target without the need of continuously pressing the drug solution. Accordingly, administration of a drug solution is facilitated, and reliability is enhanced in administrating the drug solution.

In particular, in the present embodiment, the check valve 30 is arranged on the inside of the cylindrical part 23 extending from the second surface 21T of the substrate 21. The region enclosed by the inner periphery of the cylindrical part 23 has an area substantially equal to the area of the second surface 21T of the substrate 21, in a radial cross section of the cylindrical part 23. Further, in the channel in which the drug solution flows, the channel portion configured by the cylindrical part 23 has a larger cross-sectional area than that of the through hole 24 (when there are a plurality of through holes 24, the cross-sectional area of each through hole 24). The configuration of providing the check valve 30 to such a channel portion can ensure a large space for arranging the check valve 30. Therefore, while the check valve 30 as a small-size device is provided in the drug solution injection device 10, the degree of freedom is enhanced in the size of the member, such as the valve body, configuring the check valve 30. Further, being arranged in the channel portion having a large cross-sectional area in the channel, the check valve 30 can receive the drug solution in a large area, and thus the check valve 30 operates smoothly.

Modification 1

Figure 5:
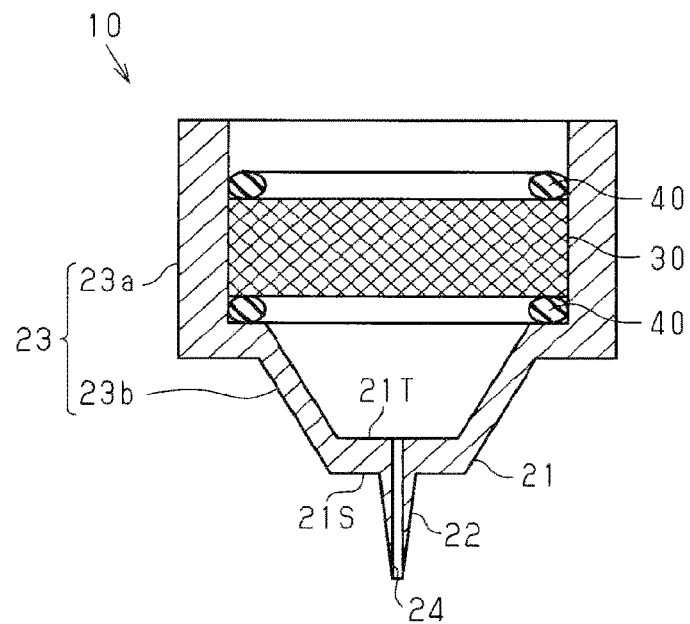
FIG. 5 is a cross-sectional view illustrating a cross-sectional structure of a drug solution injection device, according to a modification.

As shown in FIG. 5, the cylindrical part 23 may have multistage cylinders. In the example shown in FIG. 5, the cylindrical part 23 has a first cylindrical part 23a and a second cylindrical part 23b having a smaller inner diameter than the first cylindrical part 23a. The second cylindrical part 23b extends from the second surface 21T of the substrate 21 in a direction opposite to the protrusions 22, and the first cylindrical part 23a is connected to one of two ends of the second cylindrical part 23b, the one end facing the substrate 21. The inner diameter of the second cylindrical part 23b gradually increases from the substrate 21 towards the first cylindrical part 23a, while the inner diameter of the first cylindrical part 23a is constant. The inner space of the first cylindrical part 23a communicates with the inner space of the second cylindrical part 23*b*, and the first and second cylindrical parts 23*a* and 23*b*, together with the second surface 21T of the substrate 21, configure the drug solution channel communicating with the through hole 24. The check valve 30 is arranged in the inner space of the first cylindrical part 23*a*.

In this configuration, the outer peripheral surface of the first cylindrical part 23*a* is located radially outwards relative to the outer peripheral edge of the second surface 21T. Further, the region enclosed by the inner periphery of the first cylindrical part 23*a* has an area larger than the area of the second surface 21T of the substrate 21 in a radial cross section of the first cylindrical part 23*a*. Thus, a larger space is ensured for arranging the check valve 30. In particular, such a configuration is preferably used when the number of protrusions 22 is small and the size of the substrate 21 is small. In the example shown in FIG. 5, the number of protrusions 22 is one.

Modification 2

In the aforementioned embodiment and Modification 1, the check valve 30 is arranged on the inside of the cylindrical part 23 which is part of the microneedle structure 20. In place of such a configuration, the drug solution injection device 10 may include a holder for supporting the microneedle structure 20 and the check valve 30.

Figure 6:
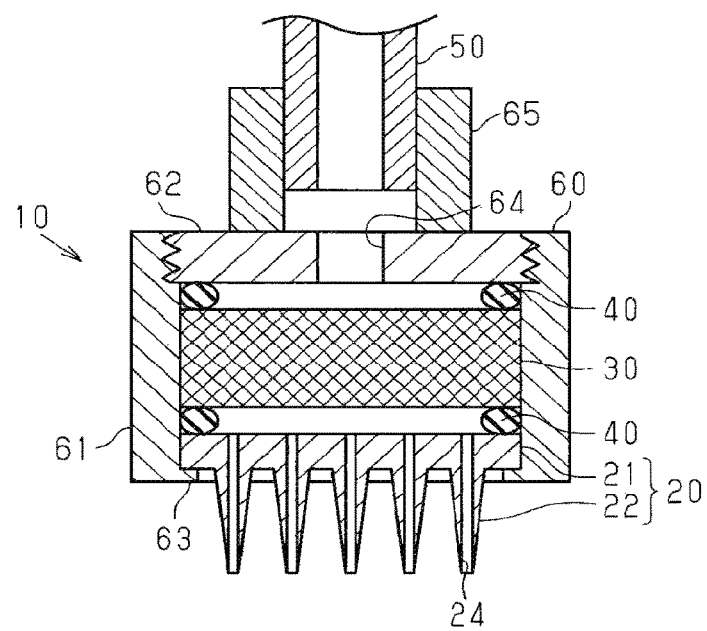
FIG. 6 is a cross-sectional view illustrating a cross-sectional structure of a drug solution injection device, according to a modification.

As shown in FIG. 6, in the configuration using a holder 60, the microneedle structure 20 does not include the cylindrical part 23. The holder 60 includes a cylindrical wall 61 which configures the drug solution channel together with the second surface 21T of the substrate 21, and a cover 62 which is fitted to one of two open ends of the cylindrical wall 61.

The cylindrical wall 61 has a lower end that is the open end opposite to the cover 62, the lower end being mounted with the microneedle structure 20. On the inside of the cylindrical wall 61, two seal members 40 and the check valve 30 sandwiched between these seal members 40 are arranged between the microneedle structure 20 and the cover 62. The lower end of the cylindrical wall 61 supports the substrate 21 so that the protrusion 22 can project out of the holder 60 from the open end.

A well-known structure for detachably assembling a member can be used as the structure for mounting the microneedle structure 20 and the check valve 30 to the cylindrical wall 61. Examples of such a configuration include a structure for fitting the objects to be attached, i.e. the microneedle structure 20 and the check valve 30, into the cylindrical wall 61, a structure for threadably fixing the objects to be attached to the cylindrical wall 61, a structure for fixing the objects to be attached to the cylindrical wall 61 by means of independent fixing screws, or by means of independent fixing screws and a presser plate, such as a washer, a structure using snap fitting, and the like. Further, a flange 63 may be formed at the lower end of the cylindrical wall 61 so as to project towards the inside of the cylindrical wall 61, while the first surface 21S of the substrate 21 of the microneedle structure 20 may be supported by the flange 63.

The cover 62 is mounted to the cylindrical wall 61 by, for example, the engagement between internal threads and external threads respectively formed in the cover 62 and the inner wall of the cylindrical wall 61. A supply hole 64 penetrating the cover 62 is formed at substantially the center of the cover 62.

When assembling the drug solution injection device 10, the microneedle structure 20, the check valve 30, and the seal member 40 are inserted into the inner space of the cylindrical wall 61 from the open end to be mounted with the cover 62, i.e. from the opening formed in the upper end of the cylindrical wall 61, in a state in which the cover 62 is detached from the cylindrical wall 61. Then, the cover 62 is mounted to the upper end of the cylindrical wall part 61.

Of the surfaces of the cover 62, the surface opposite to the surface facing the inner space of the cylindrical wall 61 may be formed with a support 65 for supporting a drug solution supply instrument, such as a syringe 50, so that the drug solution supply instrument can be mounted to the support 65. In this case, the drug solution taken from the drug solution supply instrument passes through the supply hole 64 and enters into the cylindrical wall 61.

Alternatively, a drug solution supply instrument may be directly mounted to the supply hole 64 of the cover 62, or may be mounted to the upper end of the cylindrical wall 61 without providing the cover 62 to the holder 60.

The material of the holder 60 is not specifically limited. Examples of the material for the holder 60 include plastic, glass, ceramics, metals, elastomer, and the like. In particular, plastic materials include polyethylene, polypropylene, polystyrene, polyamide, polycarbonate, cyclic polyolefin, acrylic, urethane resins, epoxy resins, and the like.

As described above, the drug solution injection device of the present embodiment obtains the advantageous effects as follows.

(1) By providing the check valve 30, the drug solution can be prevented from flowing in the direction away from the tip of the protrusion 22. Therefore, the backflow of the drug solution in the through hole 24 can be prevented.

(2) In the configuration in which the microneedle structure 20 includes the cylindrical part 23, the check valve 30 is arranged on the inside of the cylindrical part 23 having a cross-sectional area larger than the through hole 24. As a result, a large space is ensured for arranging the check valve 30, and thus the degree of freedom is enhanced in the size of the member, such as the valve body, configuring the check valve 30.

(3) In the configuration in which the microneedle structure 20 is supported by the holder 60, the area of the region enclosed by the inner peripheral surface of the cylindrical wall 61 supporting the substrate 21 is larger than the area of the second surface 21T of the substrate 21 in the radial cross section of the cylindrical wall 61. Thus, in the channel in which the drug solution flows, the channel portion configured by the cylindrical wall 61 is ensured to have a relatively large cross-sectional area. Therefore, by arranging the check valve 30 on the inside of the cylindrical wall 61 having a cross-sectional area larger than the through hole 24, a large space is ensured for arranging the check valve 30. Therefore, the degree of freedom is enhanced in the size of the member, such as the valve body, configuring the check valve 30.

(4) Since the microneedle structure 20 is made of a biocompatible material, the portion inserted into the body of an administration target has biocompatibility. Therefore, backflow of a drug solution can be prevented in the drug solution injection device 10 suitable for use in a human.

It should be noted that the aforementioned embodiment can be modified and implemented as follows.

The drug solution injection device 10 may include a plurality of seal members 40 on the upstream or downstream side of the check valve 30. With this configuration, the drug solution is prevented from leaking in a region from which the drug solution is unlikely to reach the through hole 24.

The check valve 30 and the seal member 40 may be integrally formed, so that the check valve 30, as a seal part, has the sealing function of the seal member 40. Specifically, the outer peripheral portion of the housing of the check valve 30 may be made of a material that can prevent permeation of a liquid, and can fill the gap between the housing and the cylindrical part 23 or the cylindrical wall 61. Examples of such a material include elastic materials made of various polymer materials such as a rubber material, a fluororesin, and the like, and metals, ceramics, carbon, and the like which are polished to a high accuracy.

With this configuration, a drug solution is prevented from leaking between the check valve 30 and the inner wall of the cylindrical part 23 or the cylindrical wall 61. In particular, integration of the check valve 30 and the seal member 40 can eliminate the gap between the check valve 30 and the seal member 40, and thus the effect of preventing leakage of the drug solution is enhanced.

The drug solution injection device 10 does not have to necessarily include the seal member 40, or the seal member 40 may be provided either upstream or downstream of the check valve 30. With this configuration as well, the effects stated in (1) to (4) can be obtained.

Figure 7:
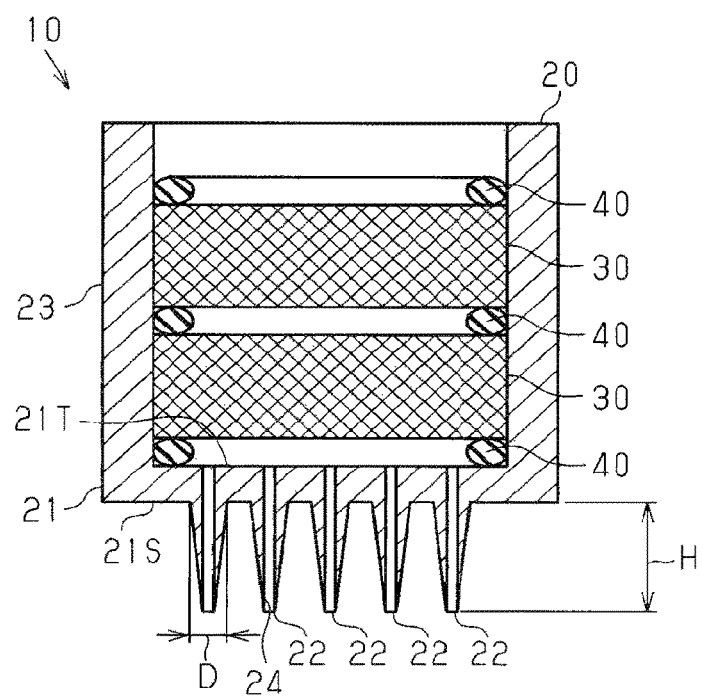
FIG. 7 is a cross-sectional view illustrating a cross-sectional structure of a drug solution injection device, according to a modification.

As shown in FIG. 7, the drug solution injection device 10 may include a plurality of check valves 30, and the plurality of check valves 30 may be serially arranged within and along the drug solution channel. The seal member 40 is preferably arranged between the adjacent check valves 30. With this configuration, each of the plurality of check valves 30 has a function of preventing the drug solution from flowing from the second surface 21T of the substrate 21 towards the check valve 30. Therefore, backflow of the drug solution can be more reliably prevented.

The check valve 30 may be arranged in a portion different from the inside of the cylindrical part 23 or the cylindrical wall 61, as long as the portion is within the drug solution channel. For example, the check valve 30 may be arranged inside the drug solution supply instrument, such as the syringe 50. In this case, the drug solution supply instrument configures part of the drug solution injection device 10. However, to prevent backflow of the drug solution in the through hole 24 positioned near the skin, the check valve 30 is preferably arranged at a position near the second surface 21T.

The aforementioned embodiment has introduced an example, as shown in FIG. 4, in which the drug solution supply instrument is directly mounted to the open end of the cylindrical part 23. Alternatively, for example, a lid-shaped member, such as the cover 62 shown in the mode including the holder 60, may be mounted to the open end of the cylindrical part 23, and the drug solution supply instrument may be mounted to this member.

EXAMPLES

The above drug solution injection device will be described by way of a specific example.

Configuration of the Drug Solution Injection Device

The drug solution injection device 10 including the microneedle structure 20, the check valve 30, the seal member 40, and the holder 60, as shown in FIG. 6, was prepared as the drug solution injection device of the present example.

The microneedle structure 20 included nine protrusions 22, with the length H of each protrusion 22 being 1.3 mm, and included the substrate 21 in a disk shape, with its outer diameter being 10 mm. The microneedle structure 20 and the holder 60 were made of polycarbonate. The check valve 30 used was of a spring disc type, as shown in FIG. 2, including the disk 31 and the spring 32 within the housing made of polycarbonate.

The microneedle structure 20 was fixed to the holder 60 by engagement of the external threads with the internal threads, and the check valve 30 was held within the cylindrical wall 61 of the holder 60 using the pressure received from the microneedle structure 20 and the seal member 40.

Drug Solution Administration Test

The syringe 50 was mounted to the support 65 of the holder 60, and then the drug solution injection device 10 and the syringe 50 were assembled to a load tester, to enable application of load and puncturing speed as desired.

A piece of skin of a 20-week-old Wistar rat was prepared as an administration target, and the hair was removed by a shaver. A physiological saline solution stained blue was prepared as a drug solution. Using the load tester, the rat's skin was punctured by the protrusions 22 of the drug solution injection device 10 with a 100 N load and at a speed of 0.01 m/s. When the puncture was stabilized, the piston of the syringe 50 was pressed to intradermally inject 50 µl of the physiological saline solution stained blue. The pressing of the piston was stopped when the amount of movement of the drug solution was indicated to be 50 µl on the scale of the syringe 50, and the state was maintained for five minutes. During the period, the piston made no movement, and no backflow of the drug solution was observed from the microneedle structure 20 towards the syringe 50. Further, during the period, gradual swelling of the skin surface was observed.

After five minutes, the drug solution injection device 10 was removed from the rat's skin. No leakage of the injected drug solution was observed on the skin surface. The rat's skin was observed with the application of transmitted light from the back surface of the skin. As a result, it was confirmed that the drug solution was injected in the skin in a range of about a 1 cm diameter.

Injection resistance of a drug solution in intradermal administration is considerably higher than the injection resistance of a drug solution in subcutaneous administration. Therefore, the injection pressure of a drug solution required for intradermal administration is larger than the injection pressure of a drug solution required for subcutaneous administration. While the drug solution is being administered using the microneedle under such high pressure conditions, for example, release of the pressing force onto the piston pressing the drug solution towards the through hole of the microneedle may cause backflow of the drug solution in the through hole. On the one hand, it is difficult to continue to push the drug solution by the pressing force such as of a piston without displacing the position of the protrusion puncturing the skin, until the administration of the drug solution is complete, specifically when the administration is performed manually.

An aspect of the present invention is to provide a drug solution injection device which prevents backflow of a drug solution in a through hole formed in a microneedle.

A drug solution injection device for solving the aforementioned problem is a microneedle that includes a substrate having a first surface and a second surface on an opposite side of the first surface, a protrusion protruding from the first surface in a direction opposite to the second surface, and a through hole penetrating from a tip of the protrusion to the second surface along a direction in which the protrusion extends. In the microneedle, the second surface includes the microneedle that configures a channel through which a drug solution flows to the through hole, and a check valve arranged inside the channel to prevent the drug solution from flowing from the second surface towards the check valve.

In the aforementioned configuration, the check valve can prevent flow of the drug solution from the second surface of the substrate towards the check valve. Thus, backflow of the drug solution is prevented in the through hole formed in the microneedle.

In the aforementioned configuration, it is preferable that the microneedle further includes a cylindrical part extending from the second surface in a direction opposite to the protrusion to configure the channel, the channel in the cylindrical part has a cross-sectional area larger than a cross-sectional area of the through hole, and the check valve is arranged inside the cylindrical part.

In the aforementioned configuration, the cylindrical part extending from the second surface of the substrate in a direction opposite to the protrusion is a portion that ensures a cross-sectional area larger than that of the through hole. Arrangement of the check valve in such a portion can ensure a larger space for arranging the check valve. Thus, the degree of freedom is enhanced in the size of the member, such as the valve body, configuring the check valve.

In the aforementioned configuration, it is preferable that the drug solution injection device further includes a cylindrical holder configuring the channel and having two open ends, wherein the channel in the holder has a cross-sectional area larger than a cross-sectional area of the through hole, one of the two open ends supports the substrate so that the protrusion protrudes out of the holder from the open end, and the check valve is arranged inside the holder.

In the aforementioned configuration, in the channel through which the drug solution flows, the portion configured by the cylindrical portion of the holder supporting the substrate can ensure a cross-sectional area larger than that of the through hole. Arrangement of the check valve in such a portion can ensure a larger space for arranging the check valve. Thus, the degree of freedom is enhanced in the size of the member, such as the valve body, configuring the check valve.

In the aforementioned configuration, it is preferable that the check valve includes a seal part that prevents the drug solution from passing between an inner wall of the channel and the check valve.

In the aforementioned configuration, the drug solution is prevented from entering between the inner wall of the channel and the check valve.

In the aforementioned configuration, it is preferable that the drug solution injection device includes a plurality of check valves, and the plurality of check valves are serially arranged within and along the channel.

In the aforementioned configuration, each of the plurality of check valves prevents the drug solution from flowing from the second surface of the substrate towards the check valve. Therefore, backflow of the drug solution is more reliably prevented.

In the aforementioned configuration, it is preferable that the microneedle is made of a biocompatible material.

In the aforementioned configuration, backflow of the drug solution is prevented by the drug solution injection device suitable for use in a human.

An embodiment of the present invention can prevent backflow of a drug solution in a through hole formed in a microneedle.

10 . . . Drug solution injection device, 20 . . . Microneedle structure, 21 . . . Substrate, 21S . . . First surface, 21T . . . Second surface, 22 . . . Protrusions, 23 . . . Cylindrical part, 24 . . . Through holes, 30 . . . Check valve, 31 . . . Disk, 32 . . . Spring, 33 . . . elastic material, 35 . . . Inflow port, 36 . . . Outflow port, 40 . . . Seal member, 50 . . . Syringe, 60 . . . Holder, 61 . . . Cylindrical wall part, 62 . . . Cover part, 63 . . . Flange part, 64 . . . Supply hole, 65 . . . Support.

Obviously, numerous modifications and variations of the present invention are possible in light of the above teachings. It is therefore to be understood that within the scope of the appended claims, the invention may be practiced otherwise than as specifically described herein.

What is claimed is:

1. An injection device, comprising:
   a microneedle structure having a channel;
   a check valve positioned in the channel of the microneedle structure; and
   an annular seal member positioned on downstream of the check valve in the channel such that the annular seal member is in contact with an outer peripheral portion of the check valve,
   wherein the microneedle structure includes a substrate and at least one protrusion formed on a first surface of the substrate such that the at least one protrusion is protruding from the first surface of the substrate and has a through hole penetrating from a tip of the at least one protrusion to a second surface of the substrate on an opposite side with respect to the first surface and configured to flow a liquid from the channel, and the annular seal member is sandwiched between the check valve and the second surface of the substrate inside the channel and enclosing an opening of the through hole.

2. The injection device of claim 1, wherein the microneedle structure has a cylindrical part which extends from the second surface in a direction opposite to the protrusion and forms the channel through which the liquid flows, and the check valve is positioned inside the cylindrical part.

3. The injection device of claim 1, further comprising:
   a cylindrical holder having two open ends and forming the channel through which the liquid flows,
   wherein the cylindrical holder has one of the two open ends configured to support the substrate such that the at least one protrusion protrudes out of the cylindrical holder from the one of the two open ends, and the check valve is positioned inside the cylindrical holder.

4. The injection device of claim 1, further comprising:
   a second check valve positioned on upstream of the check valve in the channel; and
   a second annular seal member positioned between the check valve and the second check valve.

5. The injection device of claim 2, further comprising:
   a second check valve positioned on upstream of the check valve in the channel; and
   a second annular seal member positioned between the check valve and the second check valve.

6. The injection device of claim 3, further comprising:
   a second check valve positioned on upstream of the check valve in the channel; and
   a second annular seal member positioned between the check valve and the second check valve.

7. The injection device of claim 1, further comprising:
   a second check valve serially positioned inside and along the channel through which the liquid flows.

8. The injection device of claim 2, further comprising:
   a second check valve serially positioned inside and along the channel through which the liquid flows.

9. The injection device of claim 3, further comprising:
   a second check valve serially positioned inside and along the channel through which the liquid flows.

10. The injection device of claim 4, wherein the second check valve is positioned in a series with the check valve inside and along the channel through which the liquid flows.

11. The injection device of claim 1, wherein the microneedle structure comprises a biocompatible material.

12. The injection device of claim 2, wherein the microneedle structure comprises a biocompatible material.

13. The injection device of claim 3, wherein the microneedle structure comprises a biocompatible material.

14. The injection device of claim 4, wherein the microneedle structure comprises a biocompatible material.

15. The injection device of claim 1, wherein the at least one protrusion comprises a plurality of protrusions such that the protrusions has through holes, respectively, and that the annular seal member encloses all openings of the through holes on the second surface of the substrate in the microneedle structure.

16. The injection device of claim 1, wherein the check valve is configured such that the channel through which the liquid flows opens upon receiving a forward pressure in a range of from 0.01 MPa to 0.30 MPa, and the check valve is configured to close the channel upon receiving a reverse pressure in a range of from 0.05 MPa to 0.30 MPa.

17. The injection device of claim 2, wherein the check valve is configured such that the channel opens upon receiving a forward pressure in a range of from 0.01 MPa to 0.30 MPa, and the check valve is configured to close the channel upon receiving a reverse pressure in a range of from 0.05 MPa to 0.30 MPa.

18. The injection device of claim 3, wherein the check valve is configured such that the channel opens upon receiving a forward pressure in a range of from 0.01 MPa to 0.30 MPa, and the check valve is configured to close the channel upon receiving a reverse pressure in a range of from 0.05 MPa to 0.30 MPa.

19. The injection device of claim 4, wherein each of the check valves is configured such that the channel opens upon receiving a forward pressure in a range of from 0.01 MPa to 0.30 MPa, and each of the check valves is configured to close the channel upon receiving a reverse pressure in a range of from 0.05 MPa to 0.30 MPa.

20. The injection device of claim 7, wherein each of the check valves is configured such that the channel opens upon receiving a forward pressure in a range of from 0.01 MPa to 0.30 MPa, and the check valves is configured to close the channel upon receiving a reverse pressure in a range of from 0.05 MPa to 0.30 MPa.

* * * * *